United States Patent [19]

Lindstrom et al.

[11] 4,450,102

[45] May 22, 1984

[54] SULFUR BASED METAL CLEANERS AND CORROSION INHIBITORS

[75] Inventors: Merlin R. Lindstrom; Gary D. Macdonell; Rector P. Louthan; Donald H. Kubicek, all of Bartlesville, Okla.

[73] Assignee: Phillips Petroleum Company, Bartlesville, Okla.

[21] Appl. No.: 438,553

[22] Filed: Nov. 2, 1982

[51] Int. Cl.$^3$ .................. C07C 145/00; C07C 149/26; C07D 207/12; C23G 1/18
[52] U.S. Cl. .................................. 252/542; 252/156; 252/391; 252/524; 422/13; 422/16; 548/543; 548/545; 548/551; 548/547
[58] Field of Search ............ 252/47.5, 149, 156, 252/158, 524, 542, 391; 548/543, 545, 551, 547

[56] References Cited

U.S. PATENT DOCUMENTS

| | | | |
|---|---|---|---|
| 3,096,142 | 7/1963 | Hartmark | 8/85 |
| 3,278,526 | 10/1966 | Louthan | 71/95 |
| 3,546,241 | 12/1970 | Hickner | 548/551 |
| 3,705,856 | 12/1972 | Sedliar | 252/156 |
| 3,762,873 | 10/1973 | Alink | 252/392 |

*Primary Examiner*—Dennis L. Albrecht

[57] ABSTRACT

Novel compositions are provided for the cleaning and inhibiting corrosion of metallic surfaces. The cleaning composition has an active ingredient consisting of at least one sulfur containing compound selected from the group consisting of a bis(N-2 pyrrolidonyl), an (N-2 pyrrolidonyl), or a bis(N-succinimidyl) sulfur-containing compound.

3 Claims, No Drawings

SULFUR BASED METAL CLEANERS AND CORROSION INHIBITORS

This invention relates to compositions used for the cleaning of and inhibiting corrosion on metal surfaces.

The surface cleanliness of metal surfaces is known to influence the physical and chemical properties of that surface. The surfaces of most metallic articles of manufacture are covered either by a metal oxide due to oxidation, organic residues, if annealed, or protective oils applied during fabrication. It is known to those skilled in the art that it is advantageous to remove such coatings from the metal surface prior to subsequent processing such as, for example, prior to applying a desired coating thereon in order to obtain the maximum adherence of the coating to the metal surface.

In addition, the corrosion of metal surfaces is also a problem. While corrosion has been a problem since metals were first introduced as structural materials, it is rapidly becoming a limiting factor. In the chemical industry, for example, pressures and temperatures have risen to the point where equipment that formerly lasted for years may fail in months; likewise, the initial cost of equipment and the volume of production have increased to such an extent that failure and replacement, together with the attendant loss of product and operating time, may be prohibitively expensive. Equally important is the fact that corrosion represents a waste of natural resources. An appreciable fraction of all metals produced are lost in the form of corrosion products. At one time this aspect of the problem was less important but, at present, metal is used in greater volume than ever before. Thus, the conservation of metals is an immediate necessity.

Therefore, compositions which clean as well as preclude corrosion of metal surfaces are highly desirable.

It is an object of this invention to provide novel compositions suitable for cleaning and inhibiting corrosion of metal surfaces.

Other aspects, objects, and the several advantages of this invention will be obvious to one skilled in the art from the following description and from the appended claims.

In accordance with the present invention we have discovered that an aqueous cleaning composition containing as an active ingredient at least one sulfur containing compound selected from the group consisting of a bis(N-2-pyrrolidonyl) sulfide compound, a N-2-pyrrolidonyl sulfide, sulfoxide or sulfone compound, or a bis(N-succinimidyl) sulfide compound is effective for cleaning and inhibiting corrosion of metal surfaces, particularly brass, copper, and steel.

The bis(N-2-pyrrolidonyl) sulfur-containing compounds useful within the context of this invention can be represented by the generalized formula:

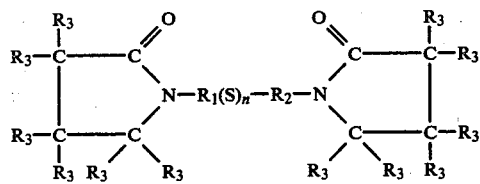

The (N-2-pyrrolidonyl) sulfur-containing compounds useful in the practice of this invention can be represented by the general formula:

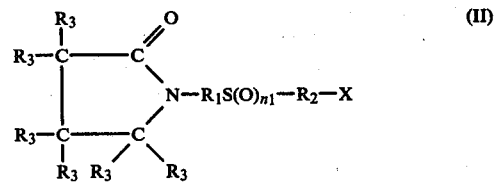

The bis(N-succinimidyl) sulfur-containing compounds useful within the context of this invention can be represented by the general formula:

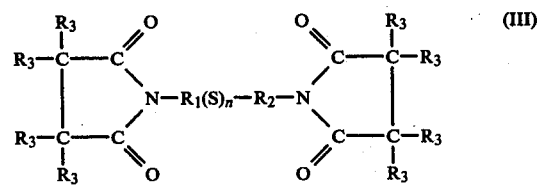

In (I), (II) and (III) above, $R_1$ can be any alkylene group having 2 to 6 carbon atoms; $R_2$ can be any alkylene radical having 1 to 6 carbon atoms; $R_3$ can be hydrogen or any alkyl radical having 1 to 3 carbon atoms; X can be hydrogen, —OH, or —COOH; n is 1 or 2, and $n_1$ is 0 or 1

Examples of compounds according to formula (I) are:
bis(2-[N-2-pyrrolidonyl]ethyl)sulfide
bis(2-[N-2-pyrrolidonyl]ethyl)disulfide
bis(2-[N-2-pyrrolidonyl]propyl)sulfide
bis(2-[N-2-pyrrolidonyl]propyl)disulfide
bis(3-[N-2-pyrrolidonyl]propyl)sulfide
bis(3-[N-2-pyrrolidonyl]propyl)disulfide
2-(N-2-pyrrolidonyl)ethyl-(N-2-pyrrolidonylmethyl)-sulfide
2-(N-2-pyrrolidonyl)ethyl-(N-2-pyrrolidonylmethyl)-disulfide
and mixtures thereof.

Examples of compounds according to formula (II) are:
2-(N-2-pyrrolidonyl)ethyl ethyl sulfide
2-(N-2-pyrrolidonyl)ethyl methyl sulfide
2-(N-2-pyrrolidonyl)propyl butyl sulfide
2-(N-2-pyrrolidonyl)ethyl-2-hydroxyethyl sulfide
2-(N-2-pyrrolidonyl)ethyl-6-hydroxyhexyl sulfide
2-(N-2-pyrrolidonyl)ethyl-2-carboxyethyl sulfide
2-(N-2-pyrrolidonyl)ethyl-3-carboxypropyl sulfide
N-(2-ethylsulfinylethyl)-2-pyrrolidone
N-(2-ethylsulfinylbutyl)-2-pyrrolidone
and mixtures thereof.

Examples of compounds according to formula (III) are:
bis(2-[N-succinimidyl]ethyl)sulfide
bis(2-[N-succinimidyl]ethyl)disulfide
bis(2-[N-succinimidyl]propyl)sulfide
bis(3-[N-succinimidyl]propyl)sulfide
and mixtures thereof.

In the case of each type of compound indicated above (I, II, and III), a general maximum total number of carbon atoms per individual compound upper limit is dictated primarily by upper feasible solubility limits of the individual compounds in the applications and processes according to the present invention.

Compounds represented by formulas I, II and III are prepared by a general method described in U.S. Pat. No. 3,278,526 whereby a substituted alkyl mercaptan is added in the presence of U.V. light and a catalyst across the double bond of a N-vinyl substituted pyrrolidone or succinimide to give as a major product the corresponding mercaptan adduct with lesser amounts of coupled products, the respective sulfides and disulfides. In the case of compounds represented by formula II, the mercaptan adduct is further treated with an oxidizing agent to give the corresponding sulfoxide or sulfone. In any event, any suitable method of preparation known in the art for making these compounds will suffice for using such in the present invention.

Generally, the aqueous cleaning composition of this invention should comprise from about 80.0 to about 99.75 wt. % water and from about 0.25 to about 20.0 wt. % of at least one of the sulfur-containing active ingredients described above.

In a presently preferred embodiment of this invention, a Group IA or IIA metal hydroxide is present in the cleaning composition. In general, when the metal hydroxide is present in a cleaning composition, the composition will comprise from about 85.0 to about 99.65 wt. % water, from about 0.1 to about 5.0 wt. % Group I or IIA metal hydroxide, and from about 0.25 to about 10.0 wt. % of at least one of the sulfur containing compounds earlier disclosed.

In a further preferred embodiment of this invention, a water soluble surfactant is employed. Any water soluble anionic, nonionic or cationic surfactant can be used in the present invention. Examples of suitable agents are anionic: alkylbenzenesulfonates for example sodium dodecylbenzenesulfonate, petroleum sulfonates and phosphate esters and salts; nonionic: ethoxylated alkyl phenols and alcohols for example octylphenoxypoly(ethyleneoxy) ethanol and carboxylic esters and amides, cationic: amines and quaternaries like stearylbenzyldimethylammonium chloride. Generally, when the water soluble surfactant is present in a cleaning composition, the composition comprises from about 80.0 to 99.55 wt. % water, from about 0.1 to 5.0 wt. % water soluble surfactant, from about 0.1 to about 5.0 wt. % Group IA or IIA metal hydroxides, and from about 0.25 to about 10.0 wt. % of at least one of the three sulfur containing compounds.

The following Examples further illustrate the present invention.

EXAMPLE I

This example describes the preparation of 2-(N-2-pyrrolidonyl)ethyl 2-hydroxyethyl sulfide, a useful ingredient in aqueous cleaning solutions. To a reactor equipped with a stirrer, thermometer, and a U.V. lamp (100 watt) was added 399.3 grams (3.59 moles) of N-vinylpyrrolidone and 280.8 grams (3.04 moles) of beta-mercaptoethanol. The reactor was closed and the stirrer and U.V. lamp turned on. The reaction was carried out without cooling between 25° C. to 33° C. over a 4.5 hour period. At the end of this time, the contents were discharged and distilled on a Vigreux column at about 200°–204° C./1 mm to give 640.2 grams of product (100 mole percent yield). Elemental analysis for $C_8H_{15}NO_2S$ were:

|  | C | H | N | O | S |
|---|---|---|---|---|---|
| % Cal'd | 50.76 | 7.99 | 7.40 | 16.91 | 16.94 |

|  | C | H | N | O | S |
|---|---|---|---|---|---|
| % Found | 50.61 | 8.02 | 7.42 | — | 16.93 |

EXAMPLE II

This example describes the preparation of 5-(N-2-pyrrolidonyl)ethyl-2-carboxyethyl sulfide. To a 5-liter steam jacketed glass flask equipped with a stirrer, condenser and dropping funnel was charged 2000 milliliters of methanol and 160 grams (4 moles) of sodium hydroxide. N-(2-Mercaptoethyl)-pyrrolidone (290 grams, 1.99 moles) was added with stirring at a rate to cause a slight reflux. After the addition was complete, a solution of 189 grams (2 moles) of chloroacetic acid dissolved in 500 milliliters of methyl alcohol was added at a rate to again cause a slight reflux. After the addition, the mixture was stirred for another 15 minutes and neutralized with 100 grams of sulfuric acid. The mixture was filtered and the filtrate vacuum stripped to remove the methyl alcohol solvent. To the residue was added 250 milliliters of toluene and the mixture filtered. The residue was stripped under vacuum to remove the toluene solvent. There was obtained 406 grams of crude residual product which was calculated to a 100 mole percent yield.

EXAMPLE III

This example describes the preparation of bis(2-[N-2-pyrrolidonyl]ethyl) disulfide, an active ingredient in aqueous cleaning solutions. To a 300 milliliter capacity autoclave was charged 121 grams (0.834 mole) of N(2-mercaptoethyl)-2-pyrrolidone, 50 milliliters of methyl alcohol, 3 grams of solid sodium hydroxide and 3 drops of cobalt 2-ethyl-hexanoate catalyst. The reactor was closed and pressured with nitrogen to 240 psig. Oxygen was then added to a total pressure of 300 psig. The stirrer was started and the temperature was maintained below 130° F. (54° C.) with internal cooling. The reaction was continued until no more oxygen pressure drop or temperature increase was noted. Three such runs were made, combined, acidified with concentrated hydrochloric acid and stripped on a rotovap. To the residue was added 300 milliliters of toluene and the mixture cooled. The solution was filtered to remove sodium chloride by-product and the toluene was stripped under vacuum to give a near quantitative yield (theoretical 241 grams) of product bis(2-[N-2-pyrrolidonyl]ethyl) disulfide. The disulfide was similarly prepared from 200 milliliters of N(2-mercaptoethyl)-2-pyrrolidone and 10 milliliters of 26 weight percent aqueous ammonium hydroxide. A still alternate procedure was conducted whereby 435 grams (3 moles) of N(2-mercaptoethyl)-2-pyrrolidone and 48 grams (1.5 moles) of elemental sulfur was heated in a 2-liter flask at 100° C. for 1 hour with stirring followed by vacuum stripping.

EXAMPLE IV

This example serves to illustrate the operability of this invention using bis pyrrolidonyl alkyl sulfides and disulfides as the active ingredients in aqueous metal surface cleaning solutions. The test used to evaluate these compounds consists of immerzing 1 inch×5 inches×0.400 inch steel, 1 inch×5 inches×0.035 inch brass, and 1 inch×5 inches×0.025 inch copper coupons into an aqueous cleaning solution containing 1 weight percent sodium hydroxide, or 1 weight percent surfactant (Triton X-202, a sodium alkylaryl polyether sulfonate), or 2 weight percent of the active sulfide or disulfide ingredient, or combinations of all three. The solutions were heated to 90° F., 140° F., or 190° F. and stirred in an ultrasonic bath. The uncleaned metal coupons were periodically removed from the bath, rinsed in running tap water, visually rated for appearance, and evaluated for cleanliness by the water break-free test. This test is discussed in Metal Finishing, 45 (12) pg. 77, 78, 88 (1947), "Testing of Alkaline Metal Cleaners" by A. Mankowich and Organic Finishing, "Method of Evaluating Alkali Cleaners," 1946, pg. 9, by C. Nielson. Water break-free test means the surface remains water-wetted without breaking away. At this point the surface is generally considered clean. The surfaces were also examined for general cleaning (e.g. tarnish) in addition to water-free. Using the procedure described, two bis(-pyrrolidonyl alkyl) thio compounds were evaluated. The data listed in Table I shows both the sulfide and disulfide compounds are active cleaning ingredients when in combination with sodium hydroxide and a surfactant. The composition is most effective in cleaning brass surfaces, fairly effective in cleaning copper surfaces and not effective in cleaning steel surfaces even at elevated temperatures. The data also shows the other ingredients, namely, sodium hydroxide and surfactant are not in themselves active cleaning agents.

TABLE I

Effect of Pyrrolidonyl Sulfide and Disulfide Derivatives in Aqueous Cleaning Solution

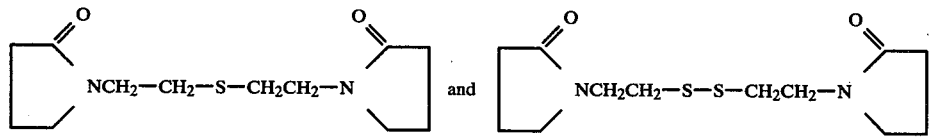

Bis(2-[N—2-Pyrrolidonyl]ethyl) Sulfate     Bis(2-[N—2-Pyrrolidonyl]ethyl) Disulfide

| | Minutes Till Cleaning and/or Break-Free[a] | | | | | | | | |
|---|---|---|---|---|---|---|---|---|---|
| | Brass | | | Copper | | | Steel | | |
| Cleaning Solution | 90° F. | 140° F. | 190° F. | 90° F. | 140° F. | 190 F. | 90° F. | 140° F. | 190° F. |
| Controls: | | | | | | | | | |
| 1. 1% Aq. NaOH | ← | ← | ← | NSC[b], Discolors | | | → | → | → |
| 2. 1%, Aq. Triton X-202[c] | ← | ← | ← | NSC, Discolors | | | → | → | → |
| 3. 1% Aq. NaOH, 1% Aq. Triton X-202 | ← | ← | ← | NSC, Discolors | | | → | → | → |
| With Above Sulfide: | | | | | | | | | |
| 4. 2% Aq. Sulfide | 15 | 15 | 10 | >15 | 15 | 10 | >15 | >15 | >15 |
| 5. 2% Aq. Sulfide, 1% NaOH | 10 | 5 | 1 | >15 | — | 5 | >15 | >15 | >15 |
| 6. 2% Aq. Sulfide, 1% NaOH, 1% X-202 | 10 | 1 | 1 | 10 | 10 | 5 | >15 | >15 | 1 Discolors |
| With Above Disulfide: | | | | | | | | | |
| 7. 2% Aq. Disulfide | >15 | >15 | >15 | ← | Discolors | → | ← | >15 | → |
| 8. 2% Aq. Disulfide, 1% NaOH | 10 | 3 | .1 | ← | Discolors | → | ← | >15 | → |
| 9. 2% Aq. Disulfide, 1% NaOH, 1% X-202 | 5 | 3 | .2 Discolors | 10 | 5 | 1 | ← | >15 | → |

[a]Break-free means the surface remains water-wetted without breaking away.
[b]Means no significant change.
[c]An alkyl aryl polyether sulfonate surfactant from Rohm and Haas.

EXAMPLE V

This example discloses the cleaning activity of five various derivatives of N-substituted 2-pyrrolidones. The procedure used to evaluate these materials is the same as that described in Example IV. The data is listed in Table II and indicates some cleaning activity with all the derivatives. However, the most active ingredients appear to be those compounds comprised of a sulfide group along with a polar end group such as hydroxy or carboxy (see Runs 4 and 5, respectively). The data also shows that oxidation of the sulfide group decreases cleaning activity (compare Run 2 with Run 3). Finally, it appears that the pyrrolidone ingredients are mostly active when used in the presence of both sodium hydroxide and a surfactant.

TABLE II

Effect of N—Substituted 2-Pyrrolidones in Aqueous Cleaning Solution

Active Ingredients:

 N—CH=CH$_2$

N—Vinyl 2-Pyrrolidone

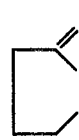 N—CH$_2$CH$_2$—S—CH$_2$CH$_3$ 2-(N—2-Pyrrolidonyl) Ethyl Ethyl Sulfide

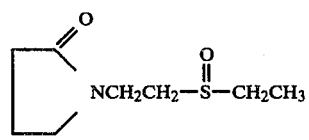 NCH$_2$CH$_2$—S(=O)—CH$_2$CH$_3$

N—(2-Ethylsulfinylethyl)-2-Pyrrolidone

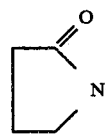 N—CH$_2$CH$_2$—S—CH$_2$CH$_2$OH 2-(N—2-Pyrrolidonyl)ethyl-2-hydroxyethyl sulfide

 N—CH$_2$CH$_2$—S—CH$_2$CH$_2$COOH 2-(N—2-Pyrrolidonyl)ethyl-2-carboxyethyl sulfide
also
5-(N—2-Pyrrolidonyl)-3-thiapentanoic acid

| | Minutes Till Cleaning and/or Break-Free | | | | | | | | |
|---|---|---|---|---|---|---|---|---|---|
| | Brass | | | Copper | | | Steel | | |
| Cleaning Solution | 90° F. | 140° F. | 190° F. | 90° F. | 140° F. | 190° F. | 90° F. | 140° F. | 190° F. |
| 1. N—Vinyl 2-Pyrrolidone (VP) | | | | | | | | | |
| A. 2% VP | ← | ← | ← | ← | NSC | → | → | → | → |
| B. 2% VP, 1% Aq. NaOH | ← | ← | Discolors | → | → | ← | NSC | → | |
| C. 2% VP, 1% Aq. NaOH, 1% X-202 | 3 | 3 | 3 | — | — | — | 10 | 10 | 10 |
| 2. 2-(N—2-Pyrrolidonyl)Ethyl Ethyl Sulfide. (EPES) | | | | | | | | | |
| A. 2%, EPES | ← | ← | ← | ← | NSC | → | → | → | → |
| B. 2% EPES, 1% Aq. NaOH | ← | ← | ← | ← | NSC | → | → | → | → |
| C. 2% EPES, 1% Aq. NaOH, 1% X-202 | NSC | 5 | 5 | 15 | 3 | 3 | 5 | 3 | 3 |
| 3. N—(2-Ethylsulfinylethyl)-2-Pyrrolidone. (ESEP) | | | | | | | | | |
| A. 2% ESEP | ← | ← | ← | ← | NSC | → | → | → | → |
| B. 2% ESEP, 1% Aq. NaOH | ← | ← | ← | ← | NSC | → | → | → | → |
| C. 2% ESEP, 1% Aq. NaOH, 1% X-202 | ← | ← | ← | NSC | → | → | >15 | 3 | 3 |
| 4. 2-(N—2-Pyrrolidonyl)ethyl-2-hydroxyethylsulfide. (PEHES) | | | | | | | | | |
| A. 2% PEHES | ← | ← | ← | ← | NSC | → | → | → | → |
| B. 2% PEHES, 1% Aq. NaOH | 5 | 5 | 1 | >15 | 10 | 10 | — | >15 | 10 |
| C. 2% PEHES, 1% Aq. NaOH, 1% X-202 | 3 to 5 | 3 to 5 | 1 | >15 | 10 | 3 | NSC | 10 | 5 |
| 5. 2-(N—2-Pyrrolidonyl)ethyl-2-carboxyethyl sulfide. (PECES) | | | | | | | | | |
| A. 2% PECES | ← | ← | ← | ← | NSC | → | → | → | → |
| B. 2% PECES, 1% Aq. NaOH | 10 | 5 | 3 | NSC | 15 | 3 | ← | NSC | → |
| C. 2% PECES, 1% Aq. NaOH | 10 | 5 | 1 | 10 | 10 | 10 | ← | 15 | → |

EXAMPLE VI

This example describes the cleaning activity of derivatives of N-(3-mercaptopropyl)succinimide. The procedure used to evaluate these materials is the same as those described in Example IV. The data listed in Table III indicates some cleaning activity from these two succinimidyl derivatives but the activity is limited to only those systems wherein sodium hydroxide and a surfactant are also present. The cleaning activity is comparable but in some cases not as good as the control using the basic compound, N-(3-mercaptopropyl)succinimide from which the inventive ingredients were derived.

TABLE III

Effect of N—(3-Mercaptopropyl)
Succinimide Derivatives in Aqueous Cleaning Solutions

Active Ingredients:
Kettle Bottoms from the distillation of

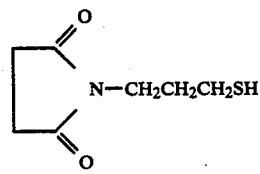

N—(3-Mercaptopropyl)Succinimide

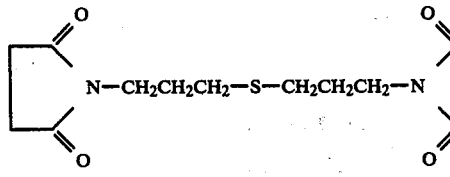

Bis(3-[N—Succinimidyl]Propyl)Sulfide

| | Immersion Time, Minutes for Cleaning or Break-Free | | | | | | | | |
|---|---|---|---|---|---|---|---|---|---|
| | Brass | | | Copper | | | Steel | | |
| Cleaning | 90° F. | 140° F. | 190° F. | 90° F. | 140° F. | 190° F. | 90° F. | 140° F. | 190° F. |
| Control: | | | | | | | | | |
| 1. N—(3-Mercaptopropyl) Succinimide. (MPS) | | | | | | | | | |
| A. 2% MPS | ← | 15 | → | ← | ← | ← | >15 | → | → |
| B. 2% MPS, 1% Aq. NaOH | 10 | 10 | 3 | 10 | 10 | 10 | ← | >15 | → |
| C. 2%, MPS, 1% Aq. NaOH, 1% X-202$^c$ | 3 | 1 | 1 | 3 | 1 | .25 | 3 | 3 | .5 |
| Invention: | | | | | | | | | |
| 2. Kettle Bottoms (KB) | | | | | | | | | |
| A. 2% KB | ← | ← | ← | ← | Insoluble | → | → | → | → |
| B. 2% KB, 1% NaOH, 1% X-202 | 5 | 5 | 1 | 5 | 10 | 3 | 3 | 10 | 1 |
| 3. Bis(3-[N—Succinimidyl] Propyl) Sulfide. (BSPS) | | | | | | | | | |
| A. 2% BSPS | ← | ← | ← | ← | Discolors | → | → | → | → |
| B. 2% BSPS, 1% Aq. NaOH | 10 | 5 | 3 | 15 | 15 | 10 | — | 15 | 15 |
| C. 2% BSPS, 1% Aq. NaOH | 10 | 10 | 3 | 15 | 15 | 3 | 3 | 3 | .5 |

EXAMPLE VII

This example describes the use of bis(2-[N-2-pyrrolidonyl]ethyl) sulfide as a copper metal corrosion inhibitor in aqueous caustic solutions. The compound has already been disclosed for application as a metal surface cleaning ingredient (see Example IV). The procedure used to evaluate compounds as corrosion inhibitors is as follows: Into screw-capped glass vials (about 4 inches×1 inch) was placed aqueous cleaning solutions (about 25 milliliters each) comprised of 2 weight percent of the active ingredient to be tested, 1 weight percent sodium hydroxide, 1 weight percent surfactant (Triton X-202, an alkyl aryl polyether sulfonate from Rohm and Haas) and 96 weight percent water and the solutions heated to 190° F. Into this solution was placed preweighed copper coupons (3 inches×0.52 inches×0.065 inches) that were precleaned by vapor degreasing, cleaned with an abrasive cleaner, water washed, acetone washed, dried and stored in a vacuum dessicator. The solutions were maintained at 90° F. for 6 hours, cooled to ambient room temperature overnight (e.g. 14 hours), reheated to 190° F. for 9.5 hours, cooled to room temperature for 14 hours, reheated to 190° F. for 3.5 hours and then removed from the vials. Deposits were brushed off, the coupons re-cleaned as previously described and re-weighed. In this manner, the corrosion rate in pounds per square foot per day were calculated for each coupon. This data is listed in Table IV where it can be seen that the inventive sulfides (Runs 5 and 6) exhibited corrosion inhibition superior to similar compounds comprised of some of the functional groups of the inventive compounds, namely hydroxy alkyl sulfide and pyrrolidone.

TABLE IV

Corrosion of Rates
of Copper at 190° F./19 Hours
Solution: 2 wt. % Inhibitor
1 wt. % NaOH
1 wt. % Surfactant
96 wt. % water

| Inhibitor | Average$^a$ Corrosion Rate, lbs/ft.$^2$/day |
|---|---|
| Controls: | |
| 1. Control (no inhibitor) | 0.0060 |
| 2. Bis(2-Hydroxyethyl) Disulfide | 1.0305 |
| 3. Bis(3-Hydroxypropyl) Disulfide | 0.6836 |
| 4. N—(2-Hydroxyethyl) Pyrrolidone | 0.0093 |
| 5. Bis(2-[N—2-Pyrrolidonyl]Ethyl) Sulfide (Invention) | 0.0047 |
| 6. Bis(2-Hydroxyethyl) Sulfide | 0.0037 |

$^a$Average of 2 samples.

SUMMARY

The data herein disclosed is summarized in Table V. The results are qualitatively rather than quantitatively listed. In general, the data suggests the bis (pyrrolidonyl) or bis (succinimidyl) sulfides or disulfides are better cleaning ingredients than the corresponding mono derivatives. Also, the data indicates the ingredients herein disclosed are most active on brass surfaces, less active on copper surfaces and least active on steel surfaces. Finally, the data suggests that some if not all of the active ingredients described might serve as copper corrosion inhibitors since one of the ingredients, bis(2-[N-2-pyrrolidonyl]ethyl) sulfide possesses copper corrosion inhibitor properties.

TABLE V

Summary
2 wt. % Ingredient
1 wt. % Sodium Hydroxide
1 wt. % Surfactant (Triton X-202)
96 wt. % Water

| Example | Ingredient | General Cleaning Activity | | |
|---|---|---|---|---|
| | | Brass | Copper | Steel |
| V | Bis(2-[N—2-Pyrrolidonyl]Ethyl) Sulfide | very good | fair | fair |
| V | Bis 2-[N—2-Pyrrolidonyl]Ethyl) Disulfide | very good | good | poor |
| VI | N—Vinyl 2-Pyrrolidone | fair | poor | poor |
| VI | 2-(N—2-Pyrrolidonyl)Ethyl Ethyl Sulfide | fair | fair | good |
| VI | N—(2-Ethylsulfinylethyl)-2-Pyrrolidone | poor | poor | fair |
| VI | 2-(N—2-Pyrrolidonyl)Ethyl-2-Hydroxyethyl Sulfide | good | fair | fair |
| VI | 2-(N—2-Pyrrolidonyl)Ethyl-2-Carboxyethyl Sulfide | good | fair | fair |
| VII | Kettle Bottoms From Distillation of N—(3-Mercaptopropyl) Succinimide | good | good | good |
| VII | Bis(3-[N—Succinimidyl]Propyl Sulfide | fair | good | good |
| VIII | Bis(2[N—2-Pyrrolidonyl]Ethyl) Sulfide as Corrosion Inhibitor | — | very good | — |

Reasonable variations and modifications are possible in the scope of the foregoing disclosure and the appended claims.

I claim:

1. An aqueous composition having as the active ingredient 2-(N-2-pyrrolidino)ethyl-2-hydroxyethyl sulfide present in an amount of from about 0.25 to 20.0 weight percent of the composition.

2. An aqueous composition having as the active ingredient 2-(N-2-pyrrolidonyl)ethyl-2-carboxylethyl sulfide present in an amount of from about 0.25 to 20.0 weight percent of the composition.

3. An aqueous composition having as the active ingredient bis(2-[N-2-pyrrolidonyl]ethyl) disulfide present in an amount of from about 0.25 to 20.0 weight percent of the composition.

* * * * *